United States Patent [19]
Cerwin et al.

[11] Patent Number: 5,341,922
[45] Date of Patent: Aug. 30, 1994

[54] PEELABLE FOIL SUTURE PACKAGING

[75] Inventors: Robert Cerwin, Pipersville, Pa.; Cheryl Trew, Somerset; Robert J. Gibbs, Flemington, both of N.J.

[73] Assignee: Ethicon, Inc., Somerville, N.J.

[21] Appl. No.: 21,814

[22] Filed: Feb. 24, 1993

[51] Int. Cl.5 ............................................. A61B 17/06
[52] U.S. Cl. ................................ 206/63.3; 206/524.9; 206/484.2
[58] Field of Search .................. 206/63.3, 524.9, 484.2

[56] References Cited

U.S. PATENT DOCUMENTS

| | | | |
|---|---|---|---|
| 2,959,280 | 11/1960 | Lloyd | 206/63.3 |
| 2,993,589 | 7/1961 | Zoller et al. | 206/63.3 |
| 3,147,861 | 9/1964 | Kurtz | 206/63.3 |
| 3,189,174 | 6/1965 | Cormack | 206/63.3 |
| 3,221,873 | 12/1965 | Bowes et al. | 206/63.3 |
| 3,256,981 | 6/1966 | Kurtz | 206/63.3 |
| 3,319,782 | 5/1967 | Bowes | 206/63.3 |
| 4,014,433 | 3/1977 | Cerwin | 206/63.3 |
| 4,699,271 | 10/1987 | Lincoln et al. | 206/63.3 |
| 5,048,678 | 9/1991 | Chambers | 206/63.3 |
| 5,129,511 | 7/1992 | Brown et al. | 206/63.3 |
| 5,213,210 | 5/1993 | Cascio et al. | 206/63.3 |
| 5,222,978 | 6/1993 | Kaplan et al. | 206/63.3 |

Primary Examiner—William I. Price
Attorney, Agent, or Firm—Susan M. Schmitt

[57] ABSTRACT

A peelable foil packaging system for absorbable or pre-moistened nylon sutures which may be used to transfer the sutures into a sterile field. In a preferred embodiment, the foil package comprises two foil sections each with a polymer inner coating. The sections are sealed together enclosing a suture holding mechanism which presents a needle with attached suture for arming a needle holder.

33 Claims, 5 Drawing Sheets

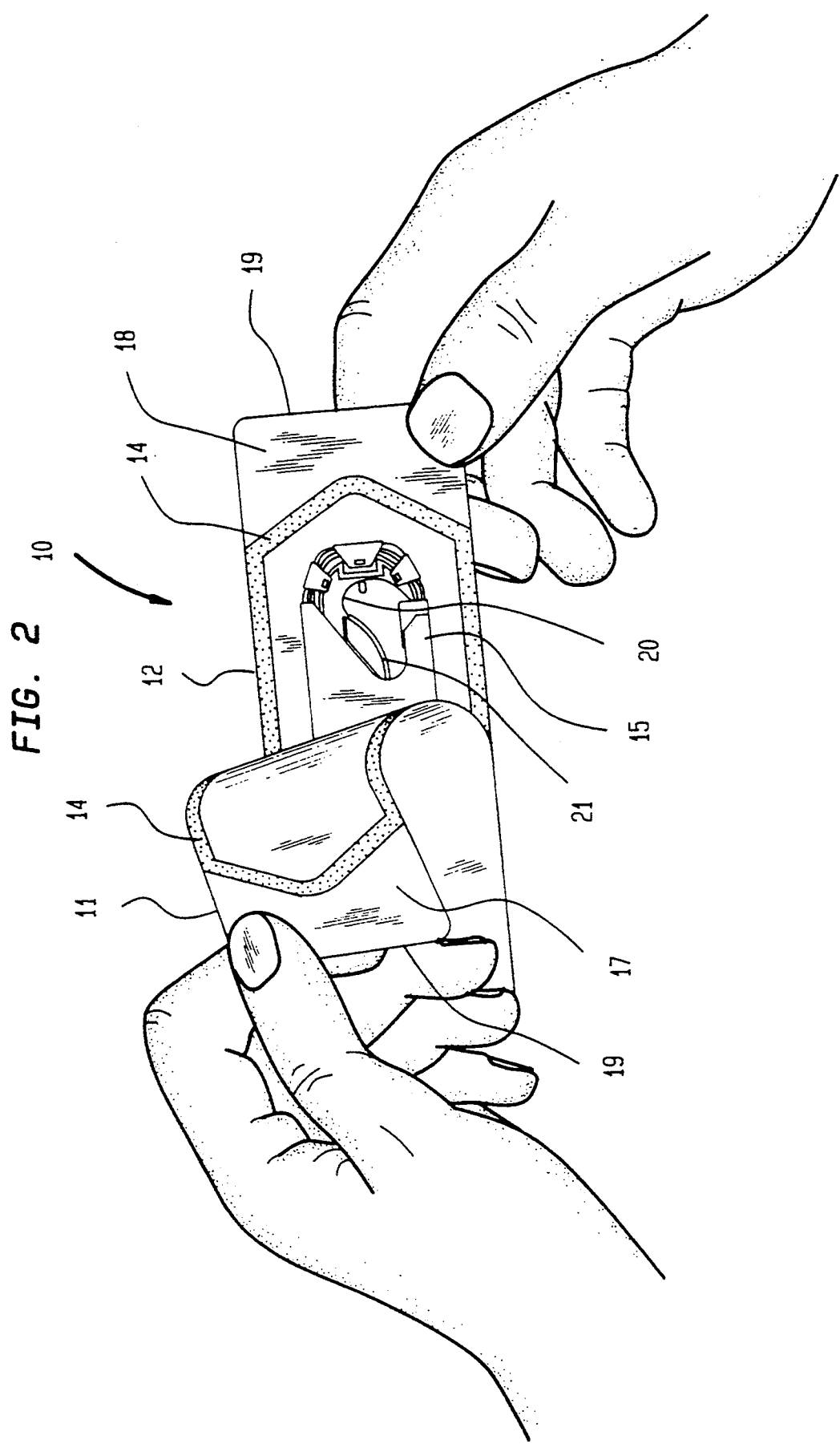

PEELABLE FOIL SUTURE PACKAGING

FIELD OF THE INVENTION

This invention relates to a peelable foil package for sutures and, in particular, for absorbable and pre-moistened nylon sutures.

BACKGROUND OF THE INVENTION

It is important for sutures to be easily and quickly supplied to sterile or scrubbed personnel working in a sterile field of use. Typically what is considered to be a sterile field is a designated area in which everything to be touched or used in surgery or a medical procedure is to remain sterile. It is important that the sterile personnel working in the sterile field do not contaminate the field by touching unsterilized packages. Therefore any suture packaging transferred into the sterile field must be sterile.

It is also important that once in the sterile field, a sterile user, can easily and quickly ready the sutures for use without compromising suture sterility.

In packaging absorbable sutures, it is important to provide a barrier to moisture and oxygen and prevent the moisture and oxygen from entering the package. It is well known that water will react with absorbable suture material to cause the polymer structure to break down. Even minute amounts of water or moisture can accelerate absorbable suture degradation. Some stability studies have indicated oxygen also may cause suture degradation.

In the packaging of hydrophilic nylon sutures, the sutures are pre-moistened and packaged in a humid environment so that the nylon material will remain pliable. It is important to provide a barrier to moisture to prevent the moisture from escaping the packaging. Thus a similar packaging is used for pre-moistened nylon sutures as is used for absorbable sutures.

Presently, both absorbable sutures and pre-moistened nylon sutures are packaged in foil and have a secondary plastic and paper overwrap. In the existing art, the foil packaging for absorbable and pre-moistened nylon sutures is made from two or more sections of foil having a polymer lamination or coating to enhance the ability of the foil to act as a sufficient barrier to moisture and oxygen. It is believed that the intimacy of the bonds of the lamination or coating with the foil plays a significant role in closing off voids in the foil. An example of polymer laminated foil suture packaging is described in U.S. Pat. No. 4,014,433.

In the prior art, the foil laminates, i.e., the foil sections with a coating and/or lamination, are heat-sealed together around their periphery forming a heat-seal around a cavity in which the sutures are contained. The process of packaging the sutures is performed in a sterile environment and the outside of the foil is sterilized as well. The secondary wrap is placed over the foil packaging to preserve the sterility of the outside of the foil packaging.

In use, the secondary wrap is typically opened or peeled apart by a non-sterile user such as a circulating nurse whose responsibility it is to get supplies and transfer them to a desired area, usually a sterile field in which surgery or a medical procedure is being performed. The non-sterile user transfers the contents of the secondary wrap by either flipping or dropping the contents, i.e., the foil packaged sutures, onto a sterile tray, or by passing the foil packaged sutures into the sterile field by peeling open the package, exposing and presenting the sterile foil package which a sterile user may then remove, e.g., by grasping with sterile forceps. The flipping, dropping or otherwise passing the secondary wrap contents may be referred to as "transferring." Once the foil package has been transferred into the sterile field, the sterile user may open the sterile foil package and, may grasp the suture needle with an attached suture.

The purpose of the secondary wrap is to enable the non-sterile user to transfer the foil packaging without touching it or otherwise compromising its sterility. It has been important for the peelable secondary packaging to have the right touch, i.e., not to require excessive force to open, so that the user has control of the transferring process, for example, to prevent the inner package component such as a tear-open foil package contained therein, from unintentionally falling out or flying away.

One of the reasons the packaging system using a foil package with a secondary wrap has been considered necessary is, if the foil were not sterile on the outside and were opened by a non-sterile user, unsterile foil, e.g., a torn or peeled outside edge, could come in contact with the suture holding mechanism or the suture and thereby compromise suture sterility.

One of the problems with the existing suture packaging is that the sterile user must open the foil package. This task can be time consuming, awkward, and inconvenient particularly in the context of surgery where a sterile user is involved in several simultaneous activities and may also be required to act quickly.

It is an object of the present invention to eliminate the use of foil suture packaging in the sterile field and to eliminate the secondary overwrap by providing a peelable foil suture package for transferring an immediately accessible suture into the sterile field. Another object of the invention is to reduce the amount of packaging material thus reducing the amount of medical waste material by eliminating the overwrap and using peelable foil to transfer a suture. Another object of the invention is to provide a sterile user easy access to a suture needle and attached suture without requiring the sterile user to peel or tear open a foil package.

Existing peelable foil suture packaging does not provide adequate barrier to moisture to prevent suture degradation for a desirable suture stability and/or is not suitable for transferring sutures into a sterile field.

It is therefore another object of the invention to provide absorbable suture packaging which provides a sufficient barrier to bacteria and moisture while facilitating a relatively easy transfer into a sterile field and easy access by a user.

It is a further object of the invention to provide a peelable foil suture package for hydrophilic nylon sutures packaged under humid conditions that is capable of preventing loss of suture moisture.

It is also an object of the present invention is to provide a peelable foil which reduces the likelihood that the user may be cut by edges of the foil packaging.

SUMMARY OF THE INVENTION

The present invention provides a peelable foil packaging system for absorbable sutures which eliminates the necessity for a secondary overwrap and eliminates the step which requires a sterile user to peel or tear open a suture package to access a suture.

The package of the present invention comprises two foil laminates. Each foil laminate of the present invention comprises a metal foil section, preferably aluminum foil, having an inner lamination comprising a polymer, such as polypropylene. The two foil laminates are sealed together enclosing a suture. The sealed foil laminates are capable of preserving sterility, preventing degradation of the suture, and maintaining suture stability by providing a sufficient barrier to moisture, oxygen and bacteria.

A laminate as used herein refers to a foil having a coating applied directly to at least one surface of a metal foil or a coating applied to at least one surface of the foil using an adhesive. A lamination is the coating applied to the foil either directly or using an adhesive. To laminate as used herein means to apply a coating directly or using an adhesive.

In one embodiment a first foil section is laminated with a first polymer coating and a second foil section is also laminated with a polymer coating. The polymer coatings of the laminates are sealable together, for example, by heat sealing or gluing. A heat sealable polymer coating is capable of forming a seal with another polymer coating when heated. Preferably, the laminates are heat-sealed together. The sealed polymer coatings of the first and second foil sections permit the foil sections to be peeled, i.e., separated, from each other. When the package is peeled, one of the coatings may separate from the foil to which it was laminated while adhering or remaining integral with the other polymer coating. The peeling may also occur in other ways, for example, the polymer coatings may separate from each other.

Two non-sealed flaps at one end of the package, one for each section of foil, may be used to peel the package open.

In a preferred embodiment of this invention, the polymer coatings for the first and second foil sections comprise polypropylene. The polypropylene is laminated on the first foil section using an extrusion coating method and on the second foil section using a dispersion coating method. The polypropylene laminated sides of the pieces of foil are heat sealed together to effect a seal substantially impervious to bacteria, water and oxygen.

Preferably the suture contained in the foil packaging is attached to a suture needle, and is wound in a suture holding mechanism which presents the needle for quick, easy grasping. An example of such suture holding mechanism is described in co-pending application entitled "NO TOUCH SUTURE PACKAGE", U.S. Ser. No. 08/008,444, filed on Jan. 19, 1993 incorporated herein by reference. Each of the two foil sections may be peeled, i.e., separated from the other, to transfer the sterile contents into a sterile field without touching or otherwise compromising the suture's sterility.

The seal strength of the package, i.e., the force per inch of seal width required to peel the package open, is sufficiently low so as to permit the user to have effective control in the transferring of the suture from the package. And, the seal strength is high enough to maintain control in the use of the package, to maintain package integrity and to minimize the risk of the package opening, particularly in transportation and handling.

Another feature of a preferred embodiment of the invention is an outer lamination comprising a polymer coating adhered to the foil with an adhesive, wherein the outer lamination and adhesive provide a "soft feel" to the package. The outer coating helps to prevent the package from cutting or scratching the user and can serve to minimize cracking and microbreaks, particularly if the packaging is mishandled. The flexibility of the package, the thickness of the foil or the coatings, or the adhesive selected to adhere the coating to the foil may effect the soft feel of the package.

Another feature of the preferred embodiment provides for a package with rounded corners to minimize cutting by the package.

The package of the present invention also may be used to package nylon sutures which are pre-moistened and packaged under humid conditions to maintain suture pliability.

DETAILED DESCRIPTION OF THE DRAWINGS

FIG. 2 is a plan view of a partially peeled foil package of the present invention containing a suture in a suture holding mechanism.

DETAILED DESCRIPTION OF THE PREFERRED EMBODIMENT

Figure 1A:
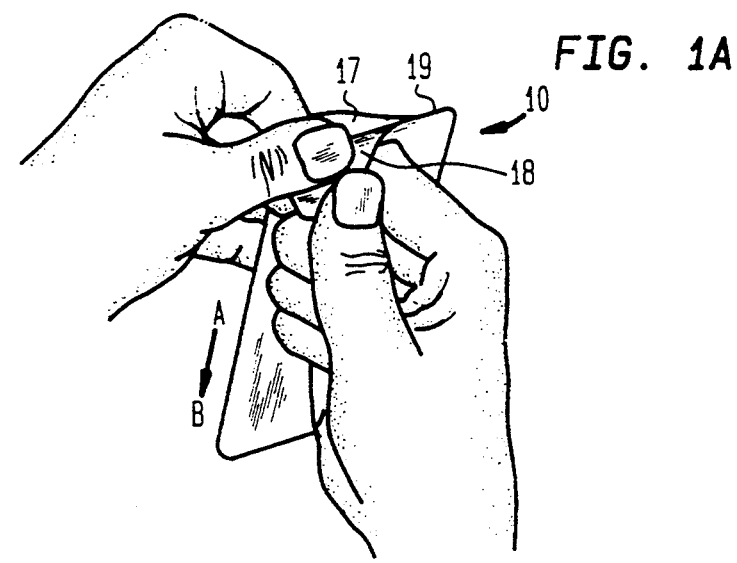
FIGS. 1A, 1B and 1C illustrate the opening of a package of the present invention and transferring a suture holding mechanism contained therein.

Referring to FIGS. 1–5, there is illustrated a package 10 in accordance with the present invention. The package 10 comprises a top foil laminate 11 and a bottom foil laminate 12. The package 10 is generally rectangular in shape to accommodate a suture holding mechanism 15 containing an absorbable suture 20 attached to a needle 21. The package 10 has rounded corners 16 to minimize sharp edges. Other shapes may be used as well.

A heat seal 14 is formed around one side 49 of the top laminate 11 and around one side 50 of the bottom laminate 12. The laminates 11 and 12 are sealed together at the heat seal 14. The suture holding mechanism 15 is packaged in a cavity 13 and is enclosed within the periphery of the heat seal 14 and between the laminates 11 and 12. The top 11 and bottom 12 laminates each additionally comprise a flap 17 and 18 respectively, extending from the heat seal 14 periphery to an end 19 of the package. The flaps 17, 18 are not heat sealed together and provide a gripping area with which the flaps can be used to peel apart the foil sections to open the package 10 and transfer the suture holding mechanism 15 into a sterile field of use.

Figure 1B:
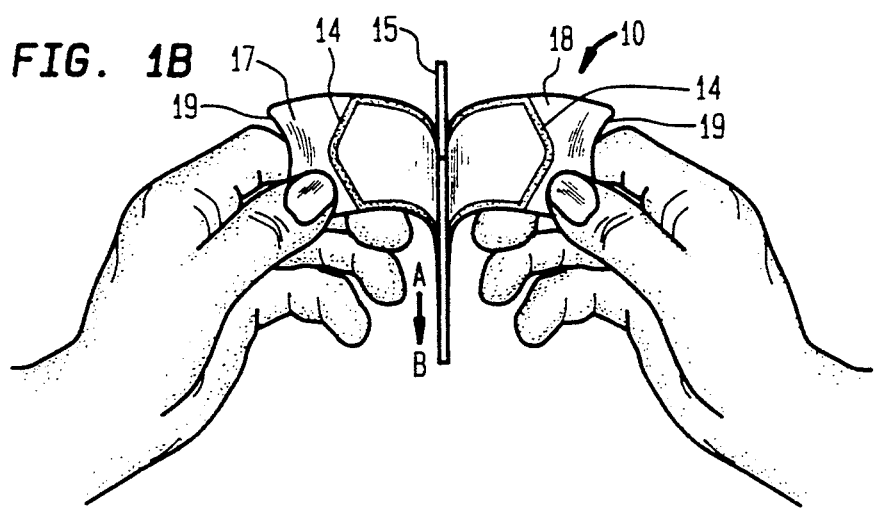
Figure 1C:
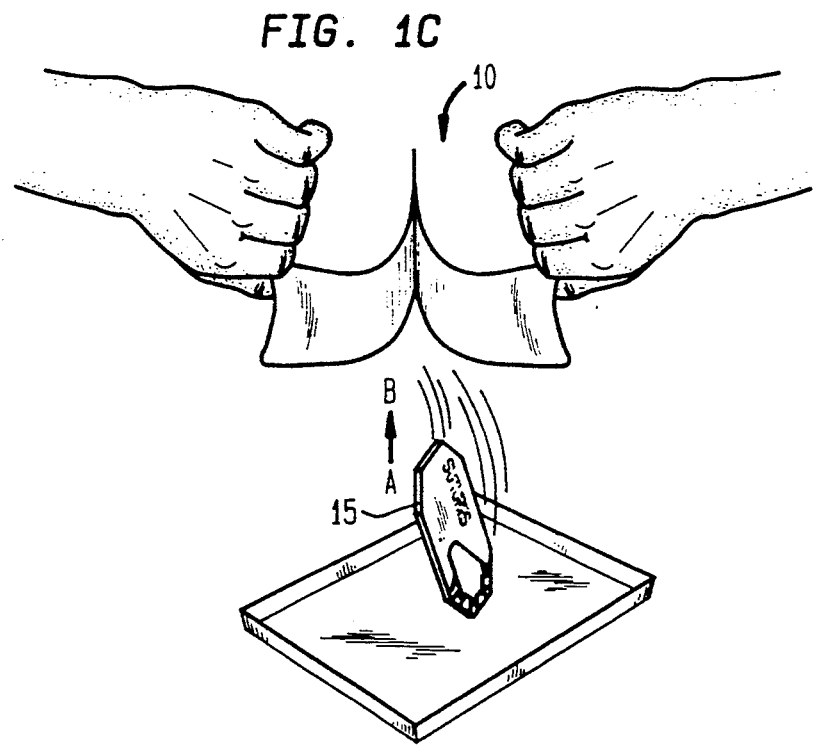

FIGS. 1A–C illustrate the package 10 in use. The flaps 17 and 18 are grasped to peel open the heat seal 14 starting at the end 19. (FIG. 1A) The package 10 is opened in a direction away from the end 19 and generally in the direction of the line AB. The flaps 17, 18 are peeled apart and away from each other to expose the suture holding mechanism 15 (FIG. 1B) while contact with the suture holding mechanism 15 is avoided. The suture holding mechanism 15 may then be transferred easily out of the opened package end by grasping the exposed suture holding mechanism, e.g., with sterile forceps (FIG. 1B) or by flipping or dropping the suture holding mechanism 15 from the foil package 10 (FIG. 1C) without contacting the suture holding mechanism 15 or the suture 20. The suture holding mechanism has labeling information 60 for the sterile user to identify the suture 20 contained therein.

Figure 3:
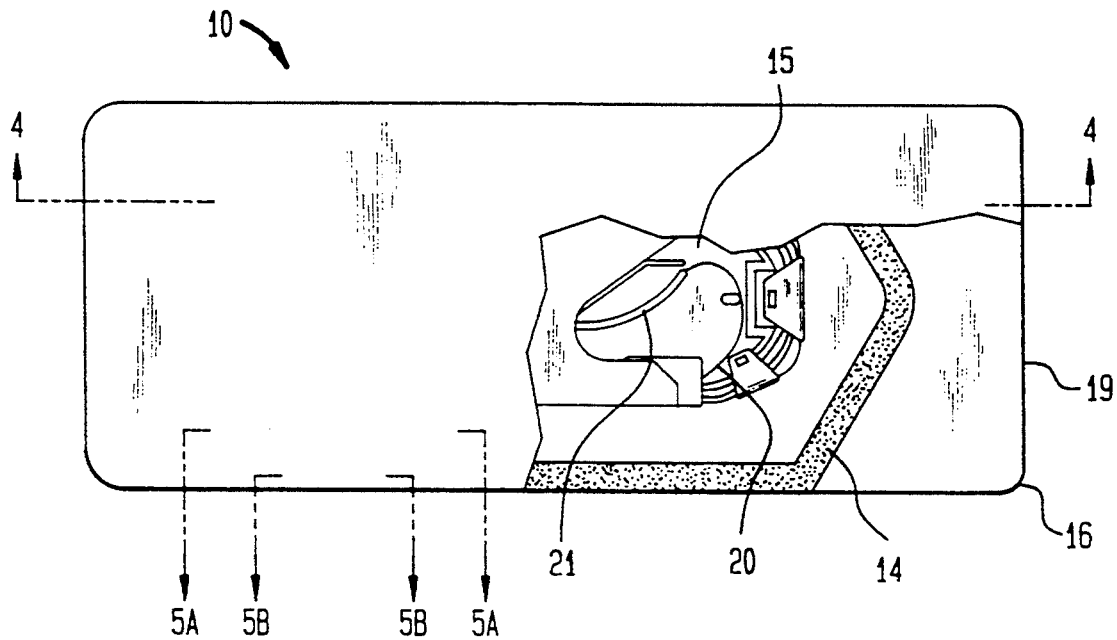
FIG. 3 is a partial outside view and a partial cross sectional view of the peelable foil package of the present invention containing a suture in a suture holding mechanism.
Figure 4:
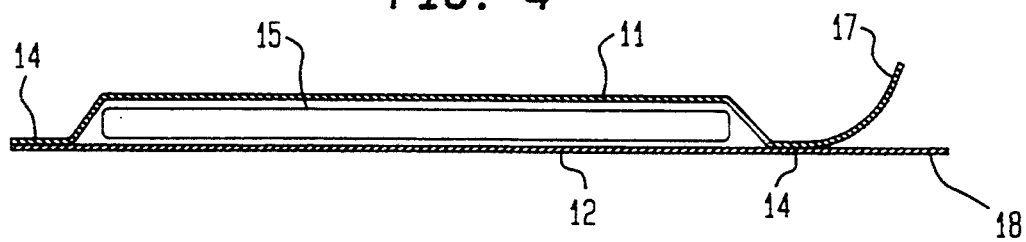
FIG. 4 is a cross sectional view taken along lines 4—4 of FIG. 3.
Figure 5A:
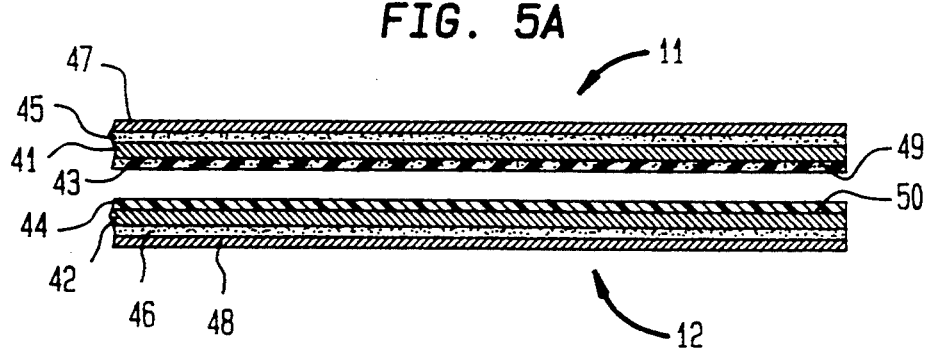
FIGS. 5A and 5B are enlarged cross sectional views of FIG. 3 taken along lines 5A—5A and 5B—5B, respectively.
Figure 5B:
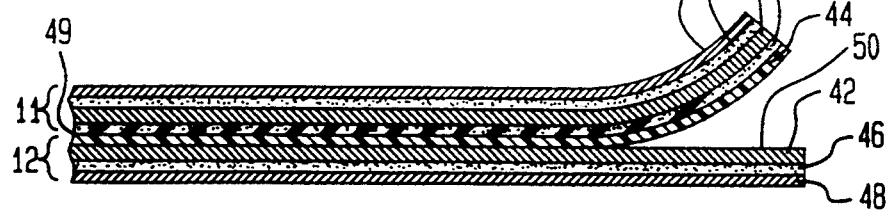

Referring to FIGS. 5A and 5B, there are illustrated enlarged cross sections along lines 5A—5A and 5B—5B of FIG. 3. FIG. 5A illustrates unsealed foil laminates. 5B illustrates sealed foil laminates as they are being peeled apart from each other. The top laminate 11 and bottom laminate 12 each comprise a metal foil section 41 and 42 respectively. The foil sections preferably comprise aluminum foil, however other metal foils are known in the art and may be used. The foil sections 41 and 42 are sufficiently thick such that when coated with a suitable polymer, they act as a barrier to moisture and oxygen and thereby prevent suture degradation. The foil sections are also sufficiently thin to provide a flexible packaging with an appropriate feel and user control when handling or opening. Ideally the foil thickness is from about 0.7 mil to about 2.0 mils and preferably from 1 mil to 1.5 mils. (1 mil is equal to 0.001 inch).

The foil section 41 is laminated on one side 49 with a polymer coating 43 and the foil section 42 is laminated on one side 50 with a polymer coating 44. The coating 43 and the coating 44 are heated at a temperature high enough to provide a seal sufficiently impervious to moisture and oxygen and low enough to avoid disturbing the integrity of the suture material. The preferred heat sealing temperature range is from 220° F. to 395° F.

Polymer laminations for foils are well known in the art. Suitable peelable foil laminates may include, for example, laminations based on polypropylene, polyester, polyethylene, and a co-polymer of polyethylene and vinyl acetate. In a preferred embodiment, the coating 43 comprises polypropylene, which is laminated onto the foil 41 using an extrusion coating method and the coating 44 comprises polypropylene which is laminated onto foil 42 using a solvent based coating method. Extrusion and solvent based methods of coating foil are well known in the art. A solvent based coating method includes solution coating methods and dispersion coating methods. In a preferred embodiment, a dispersion coating method is used. The coatings may be reversed, i.e. the top section may be coated using a solvent based coating method and the bottom section may be coated using an extrusion coating method.

Referring to FIG. 5B, as the package is peeled, i.e., the foil sections are separated, the coating 44 continues to adhere to the coating 43 by virtue of the heat sealing. The coating 44 is peelable, i.e., it at least partially separates from the foil section 42 to which it was laminated. The peel or separation of the foil sections may be affected by other means, for example, the polymer coatings may separate from each other.

It is desirable to keep the cavity 13 as small as possible so that the suture holding mechanism 15 fits snugly into the cavity 13. A snug fit allows greater control in opening the package 10. It is preferred, especially with heat sensitive sutures, that the heat sealing be spaced a distance away from the cavity 13.

Figure 8:
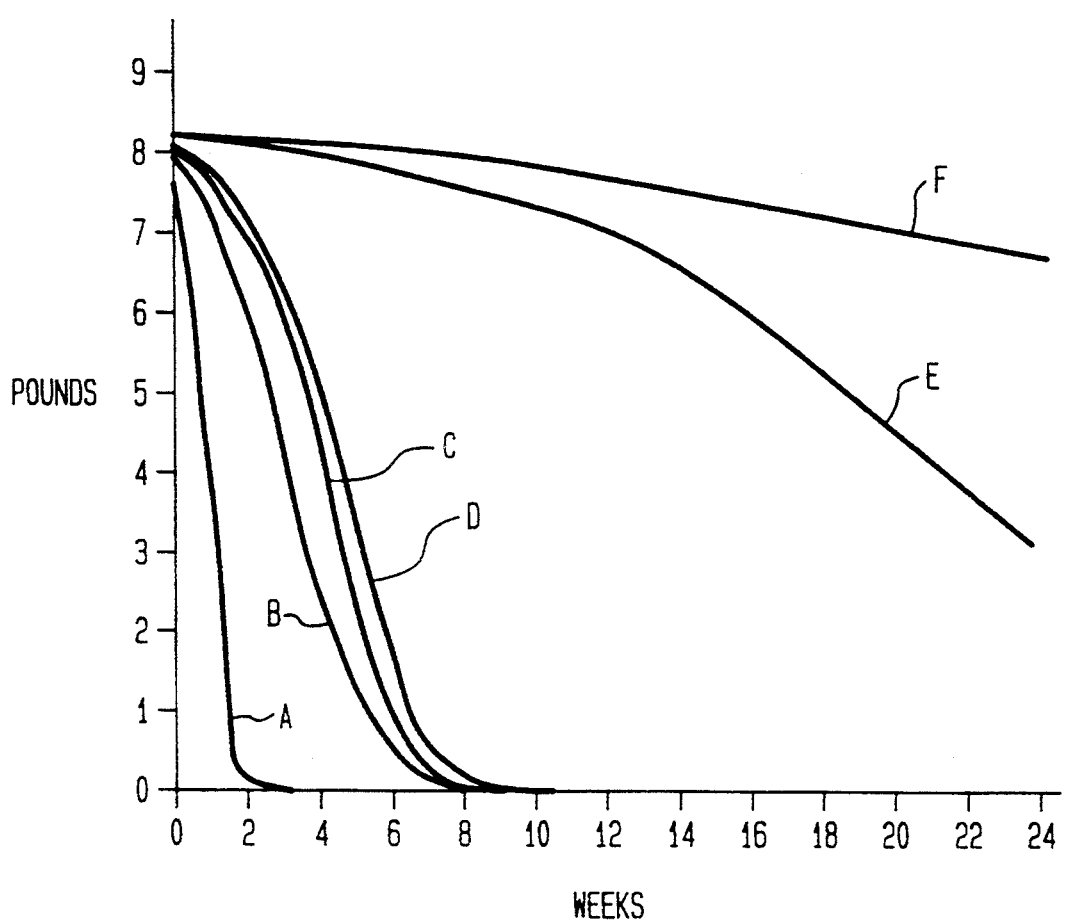
FIG. 8 is a graph representing a 24-week suture stability study.

The ability of a package to keep out moisture can be expressed as a function of the stability of sutures contained in the package under controlled environmental conditions. Stability tests are well known in the art. One measure of suture stability is breaking strength at varying time intervals under controlled conditions. FIG. 8 illustrates the results of a 24 week accelerated stability study of various foil laminates using a 12 day in vitro breaking strength test as described in Example 1 below.

EXAMPLE 1

A six month (24 week) accelerated stability study was conducted. VICRYL ™ absorbable sutures were wound in polypropylene rather than paper folders to eliminate potential distribution of moisture between suture and folder. The sutures were packaged in peelable foil single overwraps and kept under accelerated environmental conditions of 50° C. and 80% relative humidity. Every two weeks suture stability was evaluated using a 12 day in vitro test. In the 12 day in vitro test the sutures are submerged in a buffered water bath at 40.9° C.+or−0.1° C. for twelve days. The 12 day in vitro test attempts to replicate what the results of a 21 day in vivo test would be. Using an Instron Test Instrument, the breaking tensile strength was measured for sutures packaged in foils labeled A–F. Foils A–D and F are peelable foils. Using infrared spectrographic analyses, the composition of the tested foils were determined to be as follows:

| Foil A | Primarily polyester with silica based filler on surface. |
|---|---|
| Foil B | Multilaminate aluminum layer with polyester-polyethylene polyethylene/vinyl acetate/acrylic acid stearate peelable coating (outermost) (tripolymer of polyethylene/vinyl acetate/acrylic acid with stearate additive) |
| Foil C | Top and bottom - polyethylene with butadiene/styrene type additive |
| Foil D | Top - polyethylene with amide species Bottom - Ethylene-co-vinyl acetate with amide species |
| Foil E | Vinyl heat seal coating applied using a solvent solution coating method |
| Foil F | Top - polypropylene Bottom - polypropylene |

The seal between the coating 43 and coating 44, in addition to being sufficiently impervious to moisture and oxygen, permits peeling of the sections 11 and 12 from one another.

The seal strength of the package, i.e., the force per inch of seal width required to peel the package open is sufficient to enable an average user enough control in opening the package 10 to transfer the suture holding mechanism into a sterile field. A seal strength of about 2 pounds per inch of seal width or less is preferred. Also, the seal strength is preferably high enough to maintain effective control in transferring the package, to maintain package integrity and to minimize the risk of the package opening, particularly in transportation and handling. Ideally the seal strength is no less than about 0.6 pounds per inch of seal width. Seal strength may be determined as described in Example 2 below.

EXAMPLE 2

Seal strength data is taken from a Model #1401 Instron using a 10 lb load cell, 0–10 lb. full scale. One inch wide seals are tested or half inch wide seals are tested and the resulting values doubled. Two sealed surfaces are separated and the force applied is recorded as a curve on an Instron chart. The Instron curve for peelable foil is ideally rectangular in shape. The seal strength is determined by the value at the plateau of the curve. A seal strength value may be derived from the chart by drawing a perpendicular line from the midpoint of the distance from the start and the end of the curve. A horizontal line is extended at the top of the curve from the point where the perpendicular line intersects the curve. An average of the values above and below the horizontal line may then be used to determine seal strength. The seal strength was determined for 10 samples of polypropylene coated foil sections which had been heat sealed together. The first foil section was laminated using an extrusion coating method and the second section was laminated using a solvent based coating method. The measured seal strength values in terms of pounds per inch of seal width were 0.90, 0.95, 0.94, 0.85, 0.88, 0.85, 0.90, 0.90, 1.02. The average seal strength was 0.90 pounds per inch of seal width.

The foil sections 41 and 42 have an outer layer of adhesive 45 and 46 respectively. The adhesive layers 45 and 46 may comprise a solvent or solventless based adhesive. The adhesive layers 45 and 46, preferably comprised a solvent based adhesive or a hot melt adhesive, and most preferably, a urethane based or an extrusion laminated adhesive. The adhesive layer 45 and 46 each adhere an outer coating 47 and 48 respectively to the foil sheet 41 and 42 respectively.

The outer coatings 47 and 48 are preferably comprised of polypropylene about 0.25 mil to about 1 mil thick. In other preferred embodiments, the outer coating 47 or the outer coating 48 may comprise polyethylene, polyester or nylon.

The flexibility of the foil package can be described in terms of its stiffness characteristics. In a preferred embodiment the package stiffness is no more than 0.017 inch-pounds for a single foil laminate and is preferably from about 0.008 inch-pounds to 0.015 inch-pounds for each foil laminate. Package flexibility is intended to provide a softer feel to the user, minimize microbreaks in package from mishandling, and optimize control in use of the package. Package flexibility or stiffness may be determined as described in Example 3 below.

EXAMPLE 3

A model #1003 Tinius Olsen stiffness tester was used. Samples one inch by four inches were cut, folded over and heat sealed together to form a 1 inch by two inches sample. A sample was placed on the tester, clamping a portion of the sample while the remaining portion is place on a moveable platform having a polished surface measuring ½ inch by 25/32 inches long. The moveable platform is connected to a pointer. As the clamped portion is rotated to a 45° angle, the moveable portion resists the movement causing the pointer to register a value. The pointer indicates a percent value of 0.10 inch-lbs. The measured the stiffness values for a sample were averaged and then divided by two to give the stiffness of a single layer of foil laminate. The machine direction and the cross direction, i.e., perpendicular to the machine direction, were measured for each sample because stiffness may vary somewhat depending on the direction of testing.

Samples of two preferred peelable foils were tested. Samples A and B each comprised a top and bottom foil laminate. The top foil laminate had a polypropylene coating with a thickness of 10 pounds/ream±1.0 pounds, applied to a 1.5 mil thick aluminum foil section using an extrusion coating method. The bottom foil had a polypropylene coating having a thickness of 1.4 pounds/ream±0.02 pounds, applied to a 1.5 mil thick aluminum foil section using a solvent based coating method. The outer coating for each section comprised a 50 ga. thick layer of polypropylene adhered with an adhesive to the foil section. The adhesive for Sample A was a solvent applied urethane based adhesive and the adhesive for Sample B was an extrusion applied ethylene acrylic acid adhesive.

The following measurements were recorded:

TABLE I

| | A Top Section | | A Bottom Section | | B Top Section | | B Bottom Section | |
|---|---|---|---|---|---|---|---|---|
| | Machine | Cross | Machine | Cross | Machine | Cross | Machine | Cross |
| | 19 | 20 | 16 | 16 | 25 | 27 | 20 | 20 |
| | 19 | 21 | 16 | 16 | 26 | 28 | 20 | 20 |
| | 19 | 20 | 16 | 17 | 27 | 28 | 20 | 21 |
| | 20 | 20 | 16 | 16 | 27 | 27 | 19 | 20 |
| | 20 | 21 | 16 | 16 | 25 | 28 | 19 | 21 |
| | 20 | 20 | 16 | 16 | 26 | 27 | 20 | 21 |
| Average | 20% | 20% | 16% | 16% | 26% | 28% | 20% | 21% |
| × 0.1 | .020 | .020 | .016 | .016 | .026 | .028 | .020 | .028 |
| ÷ 2 = stiffness (inch = pounds) | .010 | .010 | .008 | .008 | .013 | .014 | .010 | .014 |

Figure 6:
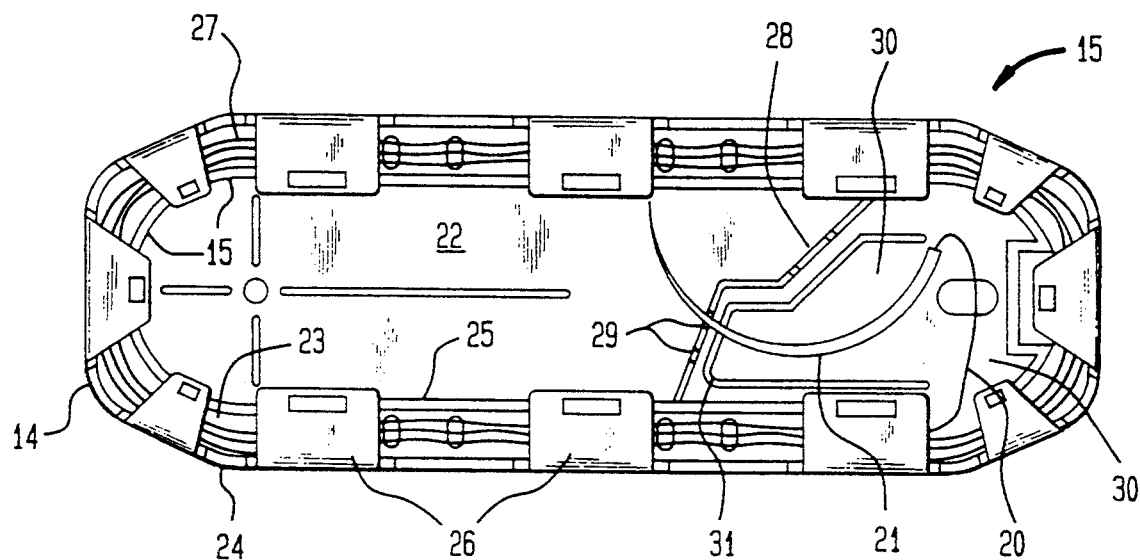
FIG. 6 is a plan view of a suture holding mechanism.
Figure 7:
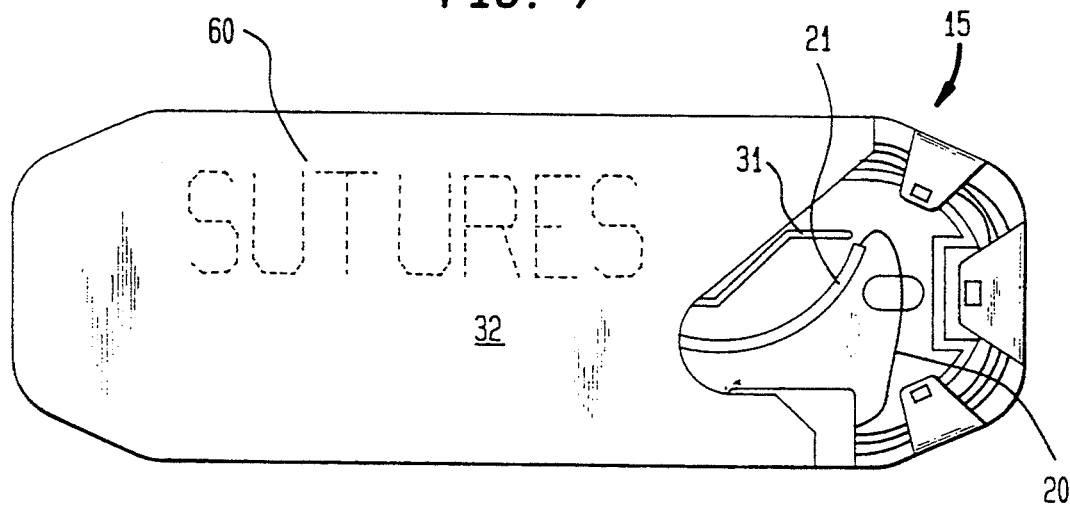
FIG. 7 is a top plan view of the suture holding mechanism depicted in FIG. 6 in a sleeve.

The suture 20 described with respect to FIGS. 1–5 is packaged in a suture holding mechanism which contains the suture and presents it for removal. A suitable suture holding mechanism is depicted in FIGS. 6 and 7. The suture holding mechanism 15 has a flat bottom section 22 with holding means 23 for one or more sutures 20 disposed around the periphery of the flat bottom section 22. The holding mechanism 15 comprises a first upwardly extending wall 24 disposed at the periphery of the flat bottom section and a second upwardly extending wall 25 disposed inwardly from the outer periphery of the holding mechanism. Spaced around the periphery are a plurality of hinged door members 26. A channel 27 is formed by the outside of the flat bottom section 22, and the inwardly spaced wall 25. The hinged door member 26 may be folded over on top of the suture 20 and locked in place. Also disposed at one end of the flat bottom section 22 is a third upwardly extending wall 28 having a plurality of cut out areas 29 for the needle 21 as shown. In practice, the suture 20 is wound about the outer periphery and in the channel 27 as previously described and the needle 21 is then placed appropriately with a portion of it being held by one of the cut out areas 29 in the third upwardly extending wall 28. Disposed beneath the needle 21 is a deflectable portion 30. The deflectable portion 30 is formed by a cut 31 in the bottom section 22 so that the deflectable portion 30 underlies the needle.

As shown in FIG. 7, the suture holding mechanism 15 depicted in FIG. 6 is encased or enclosed in a protective sleeve 32. The sleeve 32 may be made from Kraft sulfate board or similar material. The sleeve 32 overlies the top of the suture holding mechanism 15 but has a cutout at one end thereof to expose the needle 21. The sleeve may have labeling information 60 printed on it. The bottom of the sleeve includes a deflectable portion formed by a cut in the bottom of the sleeve (not shown). The deflectable portion of the sleeve is aligned with and is slightly larger than the deflectable portion 30 of the suture holding mechanism 15.

It is a simple matter when the user desires to extract the needle and suture from the package to grasp the needle with forceps. Because the area underlying the needle is deflectable, the forceps can be placed as deep as desired on the needle so that the needle only needs to be grasped once by the forceps and the needle and suture removed from the package, ready for use. Because the deflectable portion of the sleeve is slightly larger, it will prevent inadvertent dislodgement of the needle should the user happen to place a finger on the deflectable portion on the sleeve, it will not deflect the deflectable portion of the suture holder. Hence, the deflectable portions of both the suture holder and the sleeve only deflect in one direction. While the suture holding mechanism has been described with regard to FIGS. 6 and 7, other suture holding mechanisms can be used.

The peelable foil package and the suture holding mechanism together provide a one step, no touch suture and needle arming system for a sterile user. In use, a non sterile user will select a foil package containing a suture holding mechanism, peel open the package and transfer the suture holding mechanism into a sterile field. The suture holding mechanism will be labeled so a sterile user can determine if the suture is appropriate. The cut out portion of the sleeve 32 exposes at least a portion of the needle so that the needle is accessible and will be readily grasped without having to tear or remove any of the protective sleeve. Thus, a sterile user can then grasp a suture needle and remove the suture without having to peel open a foil over wrap and without having to touch the needle.

In a preferred embodiment the suture holding mechanism presents the needle so that it may easily be grasped by forceps or a needle holder used to hold a suture needle while suturing. The forceps or needle holder can deflect the bottom of the suture holding mechanism and its sleeve in one direction and obtain a good "bite" or grasp on the needle.

The invention described and the specific details and the manner in which it may be carried out having been exemplified it will be readily apparent to those skilled in the art that innumerable variations, modifications, and extensions of the basic principles involved may be made without departing from the spirit and scope of the present invention.

What is claimed is:

1. A suture package comprising
    a first laminate comprising a first foil section laminated on a first side with a first polymer coating to form a material substantially impervious to moisture;
    a second laminate comprising a second foil section laminated on a first side with a second polymer coating to form a material substantially impervious to moisture;
    wherein said first laminate and said second laminate are sealed together to form a substantially moisture impervious seal and enclose a suture between the first laminate and the second laminate and within the seal;
    wherein the first section and the second section each comprised a flap for grasping the package to peel said first section and said second section from each other;
    wherein said package may be opened to enable transferring of the suture to a desired area;
    wherein the first polymer coating and second polymer coating are heat-sealable polymers;
    wherein said first laminate and said second laminate are heat sealed together; and
    wherein the second polymer coating is peelable from the second foil section when the second polymer coating is heat sealed with the first polymer coating.

2. The suture package of claim 1 wherein the foil comprises aluminum.

3. The suture package of claim 1 wherein the first polymer coating and second polymer coating each comprise polypropylene.

4. The suture package of claim 1 wherein the first polymer coating comprises polyethylene.

5. The suture package of claim 1 wherein the first polymer coating comprises a copolymer of polyethylene and vinyl acetate.

6. The suture package of claim 1 wherein said package has rounded corners.

7. The suture package of claim 1 wherein the suture is an absorbable suture.

8. The suture package of claim 1 wherein the suture comprises a pre-moistened hydrophilic nylon material.

9. A suture package comprising
    a first laminate comprising a first foil section laminated on a first side with a first polymer coating to form a material substantially impervious to moisture;
    a second laminate comprising a second foil section laminated on a first side with a second polymer coating to form a material substantially impervious to moisture;
    wherein said first laminate and said second laminate are sealed together to form a substantially moisture impervious seal and enclose a suture between the first laminate and the second laminate and within the seal;
    wherein the first section and the second section each comprised a flap for grasping the package to peel said first section and said second section from each other;
    wherein said package may be peeled opened to enable transferring of the suture to a desired area;
    wherein said first polymer coating comprises an extrusion coated polymer; and
    wherein said second polymer coating comprises a solvent based coated polymer.

10. The suture package of claim 9 wherein the solvent based coated polymer comprises a dispersion coated polymer.

11. The suture package of claim 9 wherein the seal has a seal strength of between 0.6 and 2 pounds per inch of seal width.

12. A suture package comprising
    a first laminate comprising a first foil section laminated on a first side with a first polymer coating to form a material substantially impervious to moisture;

a second laminate comprising a second foil section laminated on a first side with a second polymer coating to form a material substantially impervious to moisture;

wherein said first laminate and said second laminate are sealed together to form a substantially moisture impervious seal and enclose a suture between the first laminate and the second laminate and within the seal;

wherein the first section and the second section each comprised a flap for grasping the package to peel said first section and said second section from each other;

wherein said package may be opened to enable transferring of the suture to a desired area;

wherein the enclosed suture is attached to a suture holding mechanism; and wherein the suture holding mechanism comprises a bottom section having a plane, and means disposed on one side of said bottom section for holding the suture and displaying the needle on said side, a portion of said bottom section underlying said needle being deflectable out of the plane of said bottom section.

13. The suture package of claim 12 wherein the suture holding mechanism further comprises a protective sleeve member enclosing said suture holding mechanism, said sleeve having a top, bottom and two longitudinal sides connecting said top and bottom, said bottom having a deflectable portion underlying the deflectable portion of said suture holding mechanism.

14. The suture package of claim 13 wherein the protective sleeve member has a cut out portion on the top of said protective sleeve for exposing said needle on said suture holding mechanism.

15. The suture package of claim 13 wherein the deflectable portion on the protective sleeve member is larger than the deflectable portion on said suture holding mechanism.

16. A suture package comprising
a first laminate comprising a first foil section laminated on a first side with a first polymer coating to form a material substantially impervious to moisture;
a second laminate comprising a second foil section laminated on a first side with a second polymer coating to form a material substantially impervious to moisture;
wherein said first laminate and said second laminate are sealed together to form a substantially moisture impervious seal and enclose a suture between the first laminate and the second laminate and within the seal;
wherein the first section and the second section each comprised a flap for grasping the package to peel said first section and said second section from each other;
wherein said package may be opened to enable transferring of the suture to a desired area
wherein the stiffness of each of the first foil laminate and the second foil laminate is not greater than 0.017 inch pounds.

17. The suture package of claim 16 wherein at least one of said first foil section and said second foil section have an outer layer of an adhesive material adhering an outer coating to said at least one of said first foil section and said second foil section.

18. The suture package of claim 17 wherein the adhesive material comprises a urethane based material.

19. The suture package of claim 17 wherein the adhesive material comprises a hot melt adhesive.

20. The suture package of claim 17 wherein the outer coating comprises polypropylene.

21. The suture package of claim 17 wherein the outer coating comprises polyethylene.

22. The suture package of claim 21 wherein the outer coating further comprises polyester and nylon.

23. The suture package of claim 17 wherein the outer coating is from 0.25 mil to 1 mil thick.

24. The suture package of claim 16 wherein the thickness of the foil sections is between 0.7 and 2.0 mils.

25. The suture package of claim 16 wherein the thickness of the foil sections is between 1 and 1.5 mil.

26. A suture arming system comprising
a suture package sufficiently moisture impervious for storage of moisture sensitive absorbable sutures, and
a sterile suture holding mechanism;
wherein said suture package comprises:
a first laminate comprising a first foil section laminated on a first side with a first polymer coating to form a material substantially impervious to moisture,
a second laminate comprising a second foil section laminated on a first side with a second polymer coating to form a material substantially impervious to moisture,
wherein said first laminate and said second laminate are sealed together to form a substantially moisture impervious seal and enclose said suture holding mechanism between the first laminate and the second laminate and within the seal,
wherein the first section and second section each comprise a flap for grasping the package to peel said first section and said second section from each other;
wherein said package is peelable to enable a non sterile user to peel said package open so that said sterile suture holding mechanism can be transferred by the non sterile user from a non sterile area to a sterile area;
wherein the sterile suture holding mechanism includes a displayed suture needle with an attached suture, said suture holding mechanism capable of being separated from said package when transferred to the sterile field and, and suture needle being immediately accessible to a sterile user for arming a needle holder when said suture holding mechanism is separated from the suture package into the sterile field.

27. The suture arming mechanism of claim 26 wherein said suture holding mechanism comprises a bottom section having a plane and means disposed on one side of bottom section for holding the suture and displaying the needle on said side, a portion of the bottom underlying said needle being deflectable out of the plane of said bottom section.

28. The suture system of claim 27 wherein said suture holding mechanism further comprises
a protective sleeve member enclosing said suture holding mechanism, said sleeve having a top, bottom, and two longitudinal sides connecting said tip and bottom, said bottom having a deflectable portion underlying the deflectable portion of said suture holding mechanism.

29. The suture system of claim 28 wherein said protective sleeve is labeled to identify the suture contained in the suture holding mechanism.

30. The suture system of claim 28 wherein the protective sleeve member has a cut out portion on the top of said protective sleeve for exposing said needle on said suture holding mechanism.

31. The suture system of claim 28 wherein the deflectable portion on the protective sleeve member is larger than the deflectable portion on the suture holding mechanism.

32. The suture system of claim 26 wherein said seal has a seal strength of from 0.6 to 2.0 pounds per inch of seal width.

33. The suture package of claim 16 wherein the seal has a seal strength of between 0.6 to 2.0 pounds per inch of seal width.

* * * * *